(12) United States Patent
Fischer et al.

(10) Patent No.: US 8,183,276 B2
(45) Date of Patent: May 22, 2012

(54) THERAPEUTIC AGENTS

(76) Inventors: Christian Fischer, Natick, MA (US); Benito Munoz, Brookline, MA (US); Alexey A. Rivkin, Boston, MA (US)

( * ) Notice: Subject to any disclaimer, the term of this patent is extended or adjusted under 35 U.S.C. 154(b) by 338 days.

(21) Appl. No.: 12/526,074

(22) PCT Filed: Feb. 5, 2008

(86) PCT No.: PCT/US2008/001503
§ 371 (c)(1), (2), (4) Date: Aug. 6, 2009

(87) PCT Pub. No.: WO2008/097538
PCT Pub. Date: Aug. 14, 2008

(65) Prior Publication Data
US 2010/0324029 A1      Dec. 23, 2010

Related U.S. Application Data

(60) Provisional application No. 60/900,200, filed on Feb. 8, 2007.

(51) Int. Cl.
| | |
|---|---|
| *A01N 43/50* | (2006.01) |
| *A61K 31/415* | (2006.01) |
| *C07D 233/00* | (2006.01) |
| *C07D 233/56* | (2006.01) |
| *C07D 233/58* | (2006.01) |

(52) U.S. Cl. .................. 514/397; 548/311.1; 548/343.5

(58) Field of Classification Search .................. 514/397; 548/311.1, 343.5
See application file for complete search history.

(56) References Cited

U.S. PATENT DOCUMENTS

| 4,012,377 | A | 3/1977 | Claisse et al. |
| 2006/0004013 | A1 | 1/2006 | Kimura et al. |
| 2007/0117798 | A1 | 5/2007 | Kimura et al. |
| 2007/0219181 | A1 | 9/2007 | Kimura et al. |
| 2009/0203916 | A1* | 8/2009 | Kushida et al. ............... 546/210 |
| 2010/0168095 | A1* | 7/2010 | Kimura et al. ............. 514/230.5 |

FOREIGN PATENT DOCUMENTS

| EP | 1808432 | 7/2007 |
| EP | 2019093 | 1/2009 |
| EP | 2019094 | 1/2009 |
| WO | WO 2006046575 | 5/2006 |

OTHER PUBLICATIONS

Ross, et al. Antiparasitic Nitoimidazoies, 3 Synthesis of 2-(4-Carboxystyr1)-5-nitro-1-vinylimidazole and related compounds, J. Med. Chem., 1973, vol. 16, pp. 347-352, p. 348, Table 1, compound 6d.

Stanek, et al., S-Adenosylmethionine Decarboxylase Inhibitors, New Aryl and Heteroaryl Analogues of Methylglyoxal Bis(guanthydrazone), J. Med. Chem., 1993, vol. 36, pp. 46-54, Scheme V, compound 18.

Couture, et al., An Expeditious Synthesis of 2-Aryl- and 2-Alkylquinazolin 4(3H)-ones Synthesis; 1991, pp. 1009-1010, p. 1009, compound 4i.

* cited by examiner

*Primary Examiner* — Sreeni Padmanabhan
*Assistant Examiner* — Sarah Pihonak
(74) *Attorney, Agent, or Firm* — Susan L. Hess; Raynard Yuro; Gerard M. Devlin

(57) ABSTRACT

The invention encompasses 2-[4-(imidazolyl)-phenyl]vinyl-heterocycle derivatives which selectively attenuate production of Abeta(1-42) and are useful in the treatment of Alzheimer's disease. Pharmaceutical compositions and methods of use are also encompassed.

7 Claims, No Drawings

THERAPEUTIC AGENTS

CROSS REFERENCE TO RELATED APPLICATIONS

This application is a U.S. National Phase application under 35 U.S.C. §371 of PCT Application No. PCT/US2008/001503, filed Feb. 5, 2008 which claims priority under 35 U.S.C. §119(e) from U.S. Provisional Application Ser. No. 60/900,200, filed Feb. 8, 2007.

This invention relates to compounds for use in therapeutic treatment of the human body. In particular, it provides compounds useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS,* 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science,* 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature,* 423 (2003), 435-9). Other proposed methods of treatment include administering a compound which blocks the aggregation of Aβ, and administering an antibody which selectively binds to Aβ.

However, recent reports (Pearson and Peers, *J. Physiol.,* 575.1 (2006), 5-10) suggest that Aβ may exert important physiological effects independent of its role in AD, implying that blocking its production may lead to undesirable side effects. Furthermore, γ-secretase is known to act on several different substrates apart from APP (e.g. notch), and so inhibition thereof may also lead to unwanted side effects. There is therefore an interest in methods of treating AD that do not suppress completely the production of Aβ, and do not inhibit the action of γ-secretase.

One such proposed treatment involves modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience,* 22 (2002), 226-54). US 2002/0015941 teaches that agents which potentiate capacitative calcium entry activity can lower Aβ(1-42).

Further classes of compounds capable of selectively attenuating Aβ(1-42) production are disclosed on WO 2005/054193, WO 2005/013985, WO 2006/008558, WO 2005/108362 and WO 2006/043064.

US 2006/0004013 and WO 2006/046575 disclose cinnamide derivatives which inhibit production of Aβ. The compounds are said to reduce the production of both Aβ(1-40) and Aβ(1-42).

The compounds of the present invention selectively attenuate production of Aβ(1-42).

According to the invention there is provided a compound of formula I:.

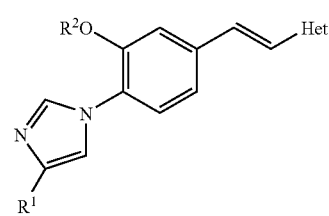

or a pharmaceutically acceptable salt or hydrate thereof; wherein:

$R^1$ represents H, $C_{1-6}$alkyl, $C_{3-6}$cycloalkyl or $C_{2-6}$alkenyl;

$R^2$ represents $C_{1-6}$alkyl, $C_{3-6}$cycloalkyl or $C_{2-6}$alkenyl;

Het represents a 5- or 6-membered unsaturated heterocyclic ring in which at least one of the ring atoms is N and at least one other ring atom is selected from N, O or S, said ring optionally being fused to an aromatic ring system of up to 10 atoms to form a fused ring system, said heterocyclic ring or fused ring system bearing 0-3 substituents selected from:

alkyl, alkenyl, alkynyl, cycloalkyl and cycloalkylalkyl groups, all of up to 10 carbon atoms, phenyl, phenyl$C_{1-4}$alkyl, naphthyl, 5- or 6-membered heterocyclyl, halogen, CN, $NO_2$, oxo, $CF_3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$, where said alkyl, alkenyl, alkynyl, cycloalkyl and cycloalkylalkyl groups bear 0-1 substituents selected from halogen, CN, $NO_2$, $CF_3$, $OR^6$, $COR^6$, $CO_2R^6$, $OCOR^5$, $N(R^6)_2$, $CON(R^6)_2$, $SR^5$, $SO_2R^5$, and $SO_2N(R^6)_2$, and said phenyl, phenylC$_{1-4}$alkyl, naphthyl and 5- or 6-membered heterocyclyl bear 0-3 substituents selected from halogen, CN, NO$_2$, R$^5$, OR$^6$, COR$^6$, CO$_2$R$^6$, OCOR$^5$, N(R$^6$)$_2$, CON(R$^6$)$_2$, SR$^5$, SO$_2$R$^5$, and SO$_2$N(R$^6$)$_2$;

R$^3$ represents C$_{1-6}$alkyl, C$_{3-6}$cycloalkyl, C$_{2-6}$alkenyl, phenyl, benzyl or CF$_3$;

R$^4$ represents H or R$^3$ or two R$^4$ groups attached to the same nitrogen atom optionally complete a heterocyclic group of up to 7 ring atoms which bears 0-3 substituents selected from halogen, CF$_3$, C$_{1-4}$alkyl, C$_{1-4}$alkoxy and C$_{1-4}$alkoxycarbonyl;

R$^5$ represents C$_{1-6}$alkyl, phenyl or CF$_3$; and

R$^6$ represents H or R$^5$ or two R$^6$ groups attached to the same nitrogen atom optionally complete a heterocyclic group of up to 7 ring atoms which bears 0-3 substituents selected from halogen, CF$_3$, C$_{1-4}$alkyl, C$_{1-4}$alkoxy and C$_{1-4}$alkoxycarbonyl.

Where a variable occurs more than once in formula I, the identity taken by said variable at any particular occurrence is independent of the identity taken at any other occurrence.

As used herein, the expression "C$_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "C$_{2-6}$alkenyl", "hydroxyC$_{1-6}$alkyl", "heteroarylC$_{1-6}$alkyl", "C$_{2-6}$alkynyl" and "C$_{1-6}$alkoxy" are to be construed in an analogous manner.

The expression "C$_{3-6}$cycloalkyl" refers to cyclic non-aromatic hydrocarbon groups containing from 3 to 6 ring carbon atoms. Examples include cyclopropyl, cyclobutyl, cyclopentenyl, cyclopentyl and cyclohexyl.

The term "heterocyclic" refers to mono- or bicyclic ring systems in which at least one ring atom is selected from N, O and S. Unless indicated otherwise, the term includes both saturated and unsaturated systems, including aromatic systems. Heterocyclic groups may be bonded via a ring carbon or a ring nitrogen, unless otherwise indicated.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of a carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the stereoisomeric forms encompassed by formula I, both optical and geometrical, fall within the scope of the invention, singly or as mixtures in any proportion.

In formula I, R$^1$ represents H, C$_{1-6}$alkyl (such as methyl, ethyl, n-propyl, isopropyl or t-butyl), C$_{3-6}$cycloalkyl (such as cyclopropyl, cyclobutyl, cyclopentyl or cyclohexyl), or C$_{2-6}$alkenyl (such as allyl). In one embodiment R$^1$ represents C$_{1-6}$ alkyl, in particular methyl.

R$^2$ represents C$_{1-6}$alkyl (such as methyl, ethyl, n-propyl, isopropyl or t-butyl), C$_{3-6}$cycloalkyl (such as cyclopropyl, cyclobutyl, cyclopentyl or cyclohexyl), or C$_{2-6}$alkenyl (such as allyl). In a particular embodiment R$^2$ represents C$_{1-6}$alkyl, in particular methyl.

Examples of heterocyclic rings and fused ring systems represented by "Het" include optionally-substituted oxazole, isoxazole, benzoxazole, thiazole, benzothiazole, oxadiazole, thiadiazole, triazole, imidazole, benzimidazole, naphthoxazole, quinazoline, thienopyrimidine and 1,7-dihydroimidazo[4,5-f]indazole.

In a subclass of the compounds of formula I Het represents:

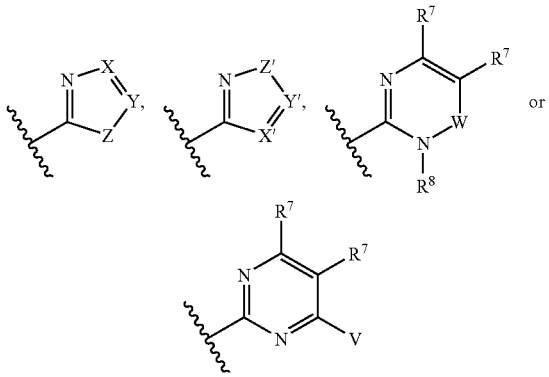

where X, X', Y and Y' each independently represents CR$^7$ or N;

Z and Z' each represents NR$^8$, O or S;
with the proviso that when Z represents O or S, at least one of X and Y represents CR$^7$, and when Z' represents O or S, Y' represents CR$^7$;

W represents C=O or SO$_2$;

V represents OR$^3$, N(R$^4$)$_2$ or SR$^3$;

each R$^7$ independently represents H or a substituent selected from:

alkyl, alkenyl, alkynyl, cycloalkyl and cycloalkylalkyl groups, all of up to 10 carbon atoms, phenyl, naphthyl, 5- or 6-membered heterocyclyl, halogen, CN, NO$_2$, CF$_3$, OR$^4$, COR$^4$, CO$_2$R$^4$, OCOR$^3$, N(R$^4$)$_2$, CON(R$^4$)$_2$, SR$^3$, SO$_2$R$^3$, and SO$_2$N(R$^4$)$_2$;

where said alkyl, alkenyl, alkynyl, cycloalkyl and cycloalkylalkyl groups bear 0-1 substituents selected from halogen, CN, NO$_2$, CF$_3$, OR$^6$, COR$^6$, CO$_2$R$^6$, OCOR$^5$, N(R$^6$)$_2$, CON(R$^6$)$_2$, SR$^5$, SO$_2$R$^5$, and SO$_2$N(R$^6$)$_2$;

and said phenyl, naphthyl and 5- or 6-membered heterocyclyl bear 0-3 substituents selected from halogen, CN, NO$_2$, R$^5$, OR$^6$, COR$^6$, CO$_2$R$^6$, OCOR$^5$, N(R$^6$)$_2$, CON(R$^6$)$_2$, SR$^5$, SO$_2$R$^5$, and SO$_2$N(R$^6$)$_2$;

or two R$^7$ groups attached to adjacent ring atoms may together represent a fused ring system consisting of a phenyl or a 5- or 6-membered heteroaryl ring which is optionally fused to a further 5- or 6-membered carbocyclic or heterocyclic ring, said fused ring system bearing 0-3 substituents selected from halogen, CN, NO$_2$, R$^3$, OR$^4$, COR$^4$, CO$_2$R$^4$, OCOR$^3$, N(R$^4$)$_2$, CON(R$^4$)$_2$, SR$^3$, SO$_2$R$^3$, and SO$_2$N(R$^4$)$_2$; and R$^8$ represents H, C$_{1-6}$alkyl, C$_{3-6}$cycloalkyl, C$_{3-6}$cycloalkylC$_{1-4}$alkyl, phenyl or benzyl wherein said phenyl and benzyl bear 0-2 substituents selected from halogen, CF$_3$ and C$_{1-4}$alkyl.

In a first embodiment, Het represents:

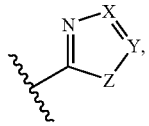

where X, Y and Z are as defined above. In a particular sub-embodiment, Z represents $NR^8$. In an alternative sub-embodiment, Z represents O or S and one of X and Y represents N and the other represents $CR^7$. In this sub-embodiment $R^7$ very suitably represents H or $C_{1-6}$alkyl, or phenyl, naphthyl or 5- or 6-membered heterocyclyl, any of which bears 0-3 substituents selected from halogen, CN, $NO_2$, $R^5$, $OR^6$, $COR^6$, $CO_2R^6$, $OCOR^5$, $N(R^6)_2$, $CON(R^6)_2$, $SR^5$, $SO_2R^5$, and $SO_2N(R^6)_2$.

Within this sub-embodiment, suitable identities for $R^7$ include phenyl, trifluoromethylphenyl, naphthyl, chlorophenyl, trifluoromethyl-3-pyridyl, dichlorophenyl, methoxyphenyl, methoxynaphthyl, bromophenyl and 1-pyrrolylphenyl.

Specific examples of compounds within this sub-embodiment include those in which $R^1=R^2=CH_3$, Z=O and X and Y are as indicated in the following table, and the pharmaceutically acceptable salts and hydrates thereof:

| X | Y | $R^7$ |
|---|---|---|
| $CR^7$ | N | 4-trifluoromethylphenyl |
| $CR^7$ | N | phenyl |
| N | $CR^7$ | 2-naphthyl |
| N | $CR^7$ | 4-chlorophenyl |
| $CR^7$ | N | 4-trifluoromethyl-3-pyridyl |
| $CR^7$ | N | 2,3-dichlorophenyl |
| $CR^7$ | N | 2-methoxyphenyl |
| $CR^7$ | N | 4-methoxy-1-naphthyl |
| $CR^7$ | N | 2-(1-pyrrolyl)phenyl |
| $CR^7$ | N | 2-trifluoromethylphenyl |
| $CR^7$ | N | 2-chlorophenyl |
| $CR^7$ | N | 2-bromophenyl |

In an alternative sub-embodiment, Het represents:

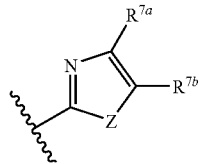

where $R^{7a}$ and $R^{7b}$ are the same or different and each represents H or $C_{1-6}$alkyl, or phenyl, naphthyl or 5- or 6-membered heterocyclyl, any of which bears 0-3 substituents selected from halogen, CN, $NO_2$, $R^5$, $OR^6$, $COR^6$, $CO_2R^6$, $OCOR^5$, $N(R^6)_2$, $CON(R^6)_2$, $SR^5$, $SO_2R^5$, and $SO_2N(R^6)_2$.

Suitable identities for $R^{7a}$ and $R^{7b}$ include H, phenyl, halophenyl, trifluoromethylphenyl and $C_{1-6}$alkyl (such as methyl, ethyl, n-propyl, isopropyl and t-butyl).

Specific examples of compounds within this sub-embodiment include those in which $R^1=R^2=CH_3$ and Z, $R^{7a}$ and $R^{7b}$ are as shown in the following table, and pharmaceutically acceptable salts and hydrates thereof:

| Z | $R^{7a}$ | $R^{7b}$ |
|---|---|---|
| O | phenyl | H |
| O | 4-fluorophenyl | H |
| O | phenyl | phenyl |
| $NCH_2Ph$ | H | H |

In a further sub-embodiment, Het represents:

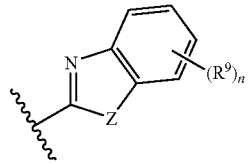

where n is 0, 1, 2 or 3; and each $R^9$ is independently selected from halogen, CN, $NO_2$, $R^3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$.

or two $R^9$ groups attached at adjacent ring positions may complete a fused benzene ring.

Most suitably, n is 0, 1 or 2.

In a particular subset, Z represents $NR^8$. Suitable identities for $R^8$ include H, $C_{1-6}$alkyl and benzyl.

Suitable identities for $R^9$ (when present) include halogen, $C_{1-6}$alkyl, $C_{1-4}$alkoxy, $NO_2$, and $SO_2N(C_{1-4}$alkyl$)_2$; or two $R^9$ groups may combine to form a fused benzene ring.

Specific examples of compounds within this sub-embodiment include those in which $R^1=R^2=CH_3$ and Z, $R^{7a}$ and $R^{7b}$ are as shown in the following table, and pharmaceutically acceptable salts and hydrates thereof:

| Z | n | $R^9$ |
|---|---|---|
| O | 2 | 4,5-benzo |
| O | 0 | — |
| NH | 0 | — |
| NH | 1 | 6-t-butyl |
| NH | 1 | 6-fluoro |
| $NCH_2Ph$ | 0 | — |
| NH | 1 | 5-nitro |
| NMe | 0 | — |
| NH | 2 | 5-Cl, 6-F |
| NH | 1 | 5-Cl |
| $NCH_2Ph$ | 1 | 5-Cl |
| NH | 1 | 7-Me |
| NH | 2 | 6,7-di-Me |
| NEt | 2 | 5,6-di-Cl |
| NH | 2 | 6,7-di-F |
| NH | 2 | 5,7-di-F |
| NH | 2 | 5,6-di-F |
| NH | 1 | 5-OMe |
| NH | 1 | $6-SO_2NEt_2$ |
| S | 0 | — |

In a second embodiment, Het represents:

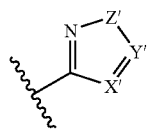

where X', Y' and Z' are as defined previously. In a particular sub-embodiment Z' represents $NR^8$ and X' and Y' independently represent $CR^7$ or N. In an alternative sub-embodiment Z' represents O or S, Y' represents $CR^7$ and X' represents $CR^7$ or N. Within this second embodiment, $R^7$ very suitably represents H or optionally substituted $C_{1-6}$alkyl, $C_{3-6}$cycloalkyl, phenyl or 5- or 6-membered heterocyclyl. Examples of suitable heterocyclyl groups represented by $R^7$ include optionally-substituted thiophene, isoxazole and pyridine.

Specific examples of compounds within this second embodiment include those in which $R^1=R^2=CH_3$ and X', Y', Z' and $R^7$ are as indicated in the following table, and pharmaceutically acceptable salts and hydrates thereof:

| X' | Y' | Z' | $R^7$ |
|---|---|---|---|
| N | $CR^7$ | O | phenyl |
| N | $CR^7$ | O | t-butyl |
| N | $CR^7$ | O | 3-thienyl |
| N | $CR^7$ | O | cyclobutyl |
| $CR^7$ | N | N-Ph | methyl |
| N | $CR^7$ | O | 3-phenyl-5-methylisoxazol-4-yl |
| $CR^7$ | N | O | H |

In a third embodiment, Het represents:

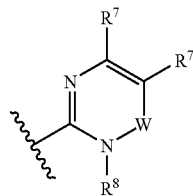

where W, $R^7$ and $R^8$ are as defined previously. Most suitably, W represents C=O. In a particular sub-embodiment, the two $R^7$ groups together represent an optionally-substituted fused ring system consisting of a phenyl or a 5- or 6-membered heteroaryl ring which is optionally fused to a further 5- or 6-membered carbocyclic or heterocyclic ring. Examples of suitable fused ring systems include benzene, naphthalene, pyridine, thiophene, dihydrocyclopenta[b]thiophene and benzofuran. Examples of suitable substituents on the fused ring system include halogen, $CF_3$, $C_{1-4}$alkyl, $C_{1-4}$alkoxy, $C_{1-4}$alkoxycarbonyl, $C_{1-4}$alkylsulfonyl, $C_{1-4}$alkylcarbonyl and di($C_{1-4}$alkyl)aminocarbonyl.

Thus in a further sub-embodiment Het represents:

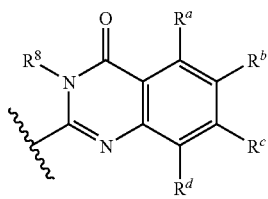

wherein $R^a$, $R^b$, $R^c$ and $R^d$ independently represent H, halogen, CN, $NO_2$, $R^3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$; or $R^a$ together with $R^b$, or $R^b$ together with $R^c$ or $R^c$ together with $R^d$ represents a fused 5- or 6-membered carbocyclic or heterocyclic ring; with the proviso that at least one of $R^a$, $R^b$, $R^c$ and $R^d$ is H; and $R^3$, $R^4$ and $R^8$ are as defined previously.

Very suitably, $R^a$, $R^b$, $R^c$ and $R^d$ independently represent H, halogen, $CF_3$, $C_{1-4}$alkyl, $C_{1-4}$alkoxy, $C_{1-4}$alkoxycarbonyl, $C_{1-4}$alkylsulfonyl or $C_{1-4}$alkylcarbonyl, provided at least one of $R^a$, $R^b$, $R^c$ and $R^d$ is H. Alternatively, $R^b$ together with $R^c$ represents a fused 5- or 6-membered carbocyclic or heterocyclic ring, e.g. a fused benzene ring.

Specific examples of compounds within this sub-embodiment include those in which $R^1=R^2=CH_3$ and $R^8$, $R^a$, $R^b$, $R^c$ and $R^d$ are as indicated in the following table, and pharmaceutically acceptable salts and hydrates thereof:

| $R^8$ | $R^a$ | $R^b$ | $R^c$ | $R^d$ |
|---|---|---|---|---|
| H | H | H | H | H |
| H | H | H | $CO_2Me$ | H |
| Ph | H | H | H | H |
| H | H | H | Cl | H |
| H | H | F | H | H |
| H | H | Cl | H | H |
| 2,6-di-MePh | Cl | H | Cl | H |
| H | F | H | H | H |
| H | H | H | $CF_3$ | H |
| H | H | Br | H | Br |
| H | H | H | $CO_2Et$ | H |
| H | H | H | Br | H |
| H | H | benzene | | H |
| H | Cl | H | Cl | H |
| H | H | H | $SO_2Me$ | H |

In an alternative sub-embodiment, Het represents:

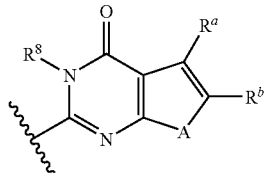

where A represents O or S;

$R^a$ and $R^b$ independently represent H, halogen, CN, $NO_2$, $R^3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$; or IV together with $R^b$ represents a fused 5- or 6-membered carbocyclic or heterocyclic ring; and $R^8$ is as defined previously.

Very suitably, $R^a$ and $R^b$ independently represent H, halogen, $CF_3$, $C_{1-4}$alkyl, phenyl, $C_{1-4}$alkylcarbonyl, $C_{1-4}$alkoxy, $C_{1-4}$alkoxycarbonyl, $C_{1-4}$alkylsulfonyl, $C_{1-4}$alkylcarbonyl or di($C_{1-4}$alkyl)aminocarbonyl, or together represent a fused 5- or 6-membered carbocyclic or heterocyclic ring, e.g. a fused benzene ring or a fused cyclopentane ring.

Specific examples of compounds within this sub-embodiment include those in which $R^1=R^2=CH_3$, $R^8$ is H, and A, $R^a$ and $R^b$ are as indicated in the following table, and pharmaceutically acceptable salts and hydrates thereof:

| A | Ra | Rb |
|---|---|---|
| S | Me | H |
| S | Me | $CONEt_2$ |
| S | Cyclopentane | |
| S | H | Ph |
| S | Me | Me |
| S | Me | COMe |
| S | Me | $CO_2Et$ |
| O | Benzene | |

Compounds of formula I may be prepared via condensation of phosphonate esters (1) with aldehydes (2):

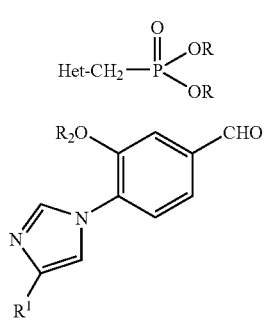

where R represents $C_{1-4}$alkyl (eg methyl) and $R^1$, $R^2$ and Het have the same meanings as before. The reaction may be carried out in an aqueous THF/ethanol mixture in the presense of alkali (eg LiOH).

Phosphonate esters (1) are obtainable by heating triethyl phosphite with Het-CH$_2$-Hal, where Hal represents Cl, Br or I and Het has the same meaning as before.

Aldehydes (2) are obtainable by reaction of imidazoles (3) with fluorobenzaldehydes (4):

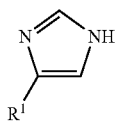

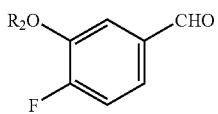

where $R^1$ and $R^2$ have the same meanings as before. The reaction takes place in DMF with heating in the presence of a base such as potassium carbonate.

Alternatively, various compounds in accordance with formula I may be obtained from cinnamic acids (5) using synthetic techniques well-known in the field of heterocyclic chemistry:

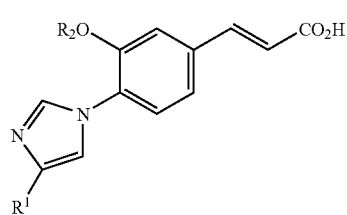

where $R^1$ and $R^2$ have the same meanings as before. For example, reaction of (5) with a 1,2-phenylenediamine (6):

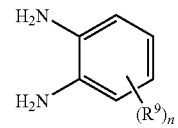

where n and $R^9$ have the same meanings as before, provides compounds of formula I in which Het represents an optionally-substituted benzimidazol-2-yl group.

Similarly, reaction of (5) with an N'-hydroxy-carboximidamide (7):

where $R^7$ has the same meaning as before, provides compounds of formula I in which Het represents a 1,2,3-oxadiazol-4-yl group.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt or hydrate thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt or hydrate thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt or hydrate thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt or hydrate thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n*. 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt or hydrate thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, autoinjector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which inhibits the aggregation of Aβ or otherwise attenuates is neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

Experimental

The ability of the compounds of Formula I to selectively inhibit production of Aβ(1-42) may be determined using the following assay:

Cell-Based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 µl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 µl of these diluted compounds in $Me_2SO$ were further diluted into 182 µl dilution buffer (phenol red-free MEM/10% FBS, 50 mM HEPES, 1% Glutamine) and 10 µl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 25 µl and 50 µl media were transferred into a standard Meso avidin-coated 96-well plate for detection of Aβ(40) and Aβ(42) peptides, respectively. 25 µl Meso Assay buffer (PBS, 2% BSA, 0.2% Tween-20) was added to the Aβ(40) wells followed by the addition of 25 µl of the respective antibody premixes to the wells:

Aβ(40) premix: 1 µg/ml ruthenylated G2-10 antibody, 4 µg/ml; and biotinylated 4G8 antibody diluted in Origen buffer Aβ(42) premix: 1 µg/ml ruthenylated G2-11 antibody, 4 µg/ml; and biotinylated 4G8 antibody diluted in Origen buffer (Biotinylated 4G8 Antibody Supplied by Signet Pathology Ltd; G2-10 and G2-11 Antibodies Supplied by Chemicon)

After overnight incubation of the assay plates on a shaker at 4° C., the Meso Scale Sector 6000 Imager was calibrated according to the manufacturer's instructions. After washing the plates 3 times with 150 µl of PBS per well, 150 µl Meso Scale Discovery read buffer was added to each well and the plates were read on the Sector 6000 Imager according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 µl of 10× MTS/PES was added to the remaining 50 µl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition of less than 10 µM and in many cases less than 1.0 µM. Furthermore, said values were were at least 2-fold lower than the corresponding $IC_{50}$ values for Aβ(1-40) inhibition, typically at least 5-fold lower, and in the preferred cases at least 50-fold lower.

EXAMPLES

In the following procedures,

"phosphonate" refers to $Het-CH_2-P(O)(OEt)_2$, prepared by heating the appropriate chloromethyl heterocycle $Het-CH_2Cl$ with triethyl phosphite;

"phosphonium salt" refers to $Het-CH_2-P(Ph)_3^+Cl^-$, prepared by heating $Het-CH_2Cl$ with triphenylphosphine in acetonitrile and collecting the resulting solid; and "aldehyde" refers to 3-methoxy-4-(4-methyl-imidazol-1-yl)-benzaldehyde.

General Procedure 1 (PG 1):

3-Methoxy-4-(4-methyl-imidazol-1-yl)-benzaldehyde, phosphonate, and lithium hydroxide hydrate were placed in a flask under nitrogen. Solvents were added and the reaction mixture stirred for 16 h at room temperature. The reaction mixture was diluted with water and extracted with ethyl acetate. The combined organic layers were washed with brine and dried over magnesium sulfate. After solvent evaporation the crude material was purified by chromatography on silica gel.

General Procedure 2 (PG 2):

3-Methoxy-4-(4-methyl-imidazol-1-yl)-benzaldehyde, phosphonium salt, and lithium hydroxide hydrate were placed in a flask under nitrogen. Solvents were added and the reaction mixture stirred for 16 h at room temperature. The reaction mixture was diluted with saturated aqueous sodium bicarbonate solution and extracted with dichloromethane. The combined organic layers were washed with brine and dried over magnesium sulfate. After solvent evaporation the crude material was purified by chromatography on silica gel.

General Procedure 3 (PG 3):

3-Methoxy-4-(4-methyl-imidazol-1-yl)-benzaldehyde, phosphonate, and lithium hydroxide hydrate were placed in a flask under nitrogen. Solvents were added and the reaction mixture stirred for 16 h at room temperature. The reaction mixture was diluted with saturated aqueous sodium bicarbonate solution and the precipitate filtered off. The obtained solid was washed with water and ether, and then dried on high vacuum. To obtain the TFA salt the product was purified by reversed phase chromatography (C18, acetonitrile/water with 0.5% TFA).

General Procedure 4 (GP 4):

(2E)-3-[3-methoxy-4-(4-methyl-1H-imidazol-1-yl)phenyl]acrylic acid (64.5 mg, 0.250 mmol), carbonyl di-imidazole (44.5 mg, 0.275 mmol), and DMF (1.325 ml) were added to a 4 ml scintillation vial and allowed to stir for 30 minutes at room temperature.

The required N-hydroxycarboximidamide (0.275 mmol) was added and the reaction mixture was allowed to stir overnight at room temperature. The contents of the vial were transferred to a 0.5-2.0 ml microwave vial and an additional 1.1 equivalents of carbonyl di-imidazole (44.5 mg, 0.275 mmol) were added. The vial was sealed and microwaved at 160° C. for 11 minutes.

Purification by reverse phase chromatography (5%-80% MeCN in water) gave the product as a white solid.

Example 1

2-{(E)-2-[3-Methoxy-4-(4-methyl-imidazol-1-yl)-phenyl]-vinyl}-4-phenyl-oxazole

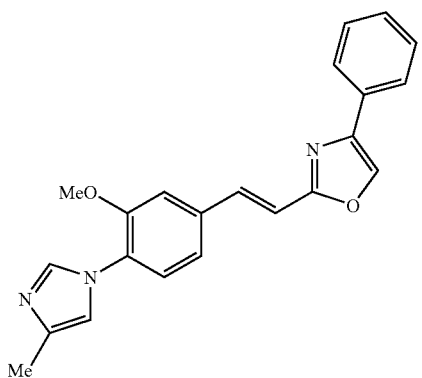

Aldehyde (22 mg, 0.1 mmol), phosphonate (33 mg, 0.11 mmol), LiOH.H$_2$O (6 mg, 0.15 mmol), and THF (1 mL) according the GP 1 gave the title compound (33 mg) as a yellow solid.

$^1$H (600 MHz, CDCl$_3$): 2.28 (s, 3H), 3.87 (s, 3H), 6.92 (s, 1H), 6.99 (d, J=16.8 Hz, 1H), 7.16 (s, 1H), 7.17 (d, J=8.1 Hz, 1H), 7.23 (d, J=8.1 Hz, 1H), 7.31 (t, J=7.5 Hz, 1H), 7.39 (t, J=7.5 Hz, 2H), 7.52 (d, J=16.8 Hz, 1H), 7.72 (s, 1H), 7.74 (d, J=7.8 Hz, 2H), 7.88 (s, 1H).

LCMS (ESI): calcd for C$_{22}$H$_{20}$N$_3$O$_2$ [M+H]$^+$ 358.2, found 358.2.

Example 2

2-{(E)-2-[3-Methoxy-4-(4-methyl-imidazol-1-yl)-phenyl]-vinyl}-4,5-diphenyl-oxazole

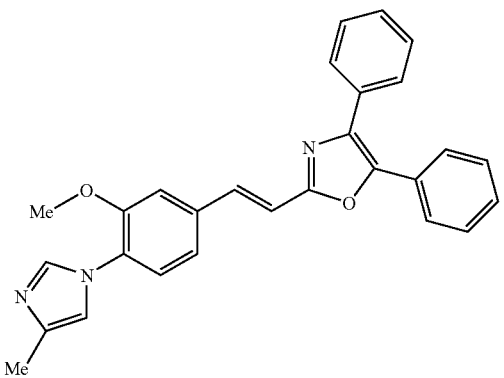

Aldehyde (140 mg, 0.650 mmol), phosphonate (297 mg, 90%, 0.720 mmol), LiOH.H$_2$O (82 mg, 1.9 mmol), THF (4.5 mL), and ethanol (1.5 mL) according the GP 1 gave the title compound (118 mg) as a yellow solid after recrystallization from ethyl acetate.

$^1$H (600 MHz, dmso-d6): 2.13 (s, 3H), 3.90 (s, 3H), 7.16 (t, J=1.2 Hz, 1H), 7.38-7.48 (m, 9H), 7.61-7.68 (m, 6H), 7.80 (s, 1H).

LCMS (ESI): calcd for C$_{28}$H$_{24}$N$_3$O$_2$ [M+H]$^+$ 434.2, found 434.2.

Example 3

5-tert-Butyl-3-{(E)-2-[3-methoxy-4-(4-methyl-imidazol-1-yl)-phenyl]-vinyl}-1,2,4-oxadiazole

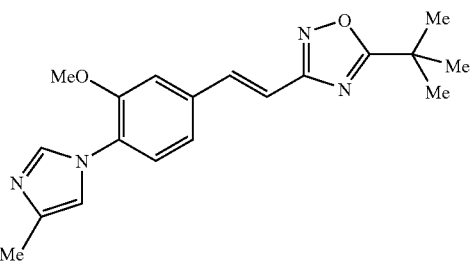

Aldehyde (250 mg, 1.16 mmol), phosphonate (383 mg, 1.39 mmol), LiOH.H$_2$O (146 mg, 3.47 mmol), THF (6 mL), and ethanol (2 mL) according the GP 1 gave the title compound (118 mg) as a colorless solid after recrystallization from ethyl acetate/hexane.

$^1$H (600 MHz, dmso-d6): 1.41 (s, 9H), 2.13 (s, 3H), 3.88 (s, 3H), 7.14 (s, 1H), 7.38 (d, J=7.9 Hz, 1H), 7.41-7.43 (m, 3H), 7.63-7.66 (m, 2H), 7.79 (d, J=1.5 Hz, 1H).

LCMS (ESI): calcd for C$_{19}$H$_{23}$N$_4$O$_2$ [M+H]$^+$ 339.2, found 339.2.

Example 4

2-{(E)-2-[3-Methoxy-4-(4-methyl-imidazol-1-yl)-phenyl]-vinyl}-1H-benzimidazole

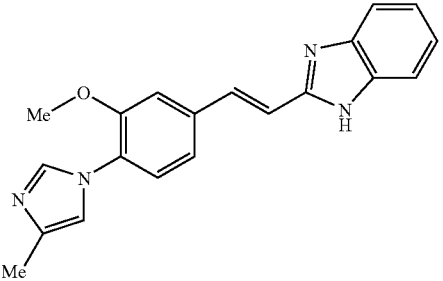

Aldehyde (150 mg, 0.69 mmol), phosphonium salt (357 mg, 0.83 mmol), LiOH.H$_2$O (87 mg, 2.08 mmol), THF (4.5 mL), and ethanol (1.5 mL) according the GP 2 gave the title compound (178 mg) as a colorless solid after recrystallization from ethyl acetate.

$^1$H (600 MHz, dmso-d6): 2.14 (s, 3H), 3.90 (s, 3H), 7.15-7.17 (m, 3H), 7.29-7.34 (m, 3H), 7.39-7.41 (m, 3H), 7.66 (d, J=16.4 Hz, 1H), 7.80 (s, 1H).

LCMS (ESI): calcd for C$_{20}$H$_{19}$N$_4$O [M+H]$^+$ 331.1, found 331.1.

Example 5

6-tert-Butyl-2-{(E)-2-[3-methoxy-4-(4-methyl-imidazol-1-yl)-phenyl]-vinyl}-1H-benzimidazole trifluoroacetate salt

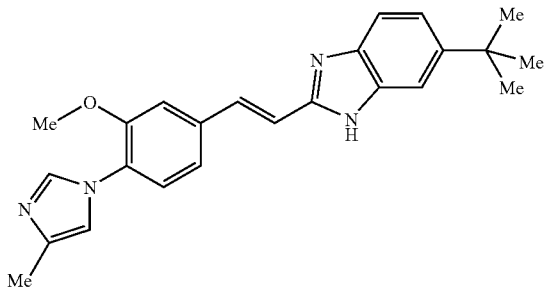

(E)-3-[3-Methoxy-4-(4-methyl-imidazol-1-yl)-phenyl]-acrylic acid (300 mg, 1.162 mmol) and 4-tert-butyl-benzene-1,2-diamine (191 mg, 1.162 mmol) were placed in a 10-mL flask under nitrogen. Ethylene glycol (2 ml) was added and the reaction mixture heated to 185° C. for 3 h and then to 170° C. overnight. The reaction was quenched with water and the precipitated green solid collected. The solid was dried on high vacuum, then recrystallized from ethyl acatate (15 mL). The residue was purified by preparative HPLC Reverse phase (C-18), eluting with Acetonitrile/Water+0.05% TFA, to give the product (266 mg) as a yellow solid.

$^1$H (600 MHz, dmso-d6): 1.33 (s, 9H), 2.14 (s, 3H), 3.90 (s, 3H), 7.06-7.78 (m, 11H).

LCMS (ESI): calcd for $C_{24}H_{27}N_4O$ [M+H]$^+$ 387.2, found 387.2.

Example 6

6-Fluoro-2-{(E)-2-[3-methoxy-4-(4-methyl-imidazol-1-yl)-phenyl]-vinyl}-1H-benzimidazole

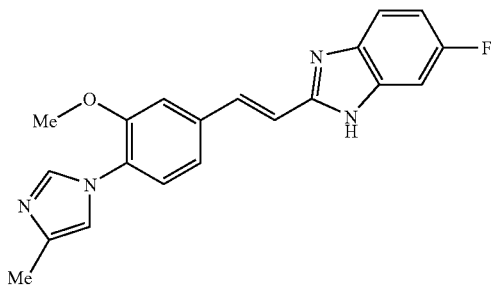

(E)-3-[3-Methoxy-4-(4-methyl-imidazol-1-yl)-phenyl]-acrylic acid (100 mg, 0.39 mmol) and 4-fluorobenzene-1,2-diamine (49 mg, 0.39 mmol) were placed in a 4-mL vial. Ethylene glycol (1 ml) was added and the reaction mixture heated to 100° C. for 16 h and then to 165° C. overnight.

The reaction was quenched with water, extracted with dichloromethane (3×20 mL) and the combined organic layers dried over magnesium sulfate. The solvent was evaporated and the obtained solid recrystallized from ethyl acatate (8 mL) to give the product (24 mg) as an orange solid.

$^1$H (600 MHz, dmso-d6): 2.14 (s, 3H), 3.90 (s, 3H), 7.02-7.79 (m, 11H).

LCMS (ESI): calcd for $C_{20}H_{18}FN_4O$ [M+H]$^+$ 349.1, found 349.1.

Example 7

2-{(E)-2-[3-Methoxy-4-(4-methyl-imidazol-1-yl)-phenyl]-vinyl}-6-nitro-1H-benzimidazole

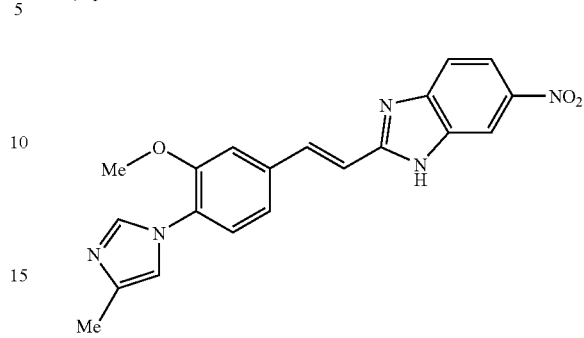

Aldehyde (100 mg, 0.46 mmol), phosphonium salt (263 mg, 0.56 mmol), LiOH.H$_2$O (58 mg, 1.39 mmol), THF (3 mL), and ethanol (3 mL) according the GP 2 gave the title compound (66 mg) as a yellow solid.

$^1$H (600 MHz, dmso-d6): 2.14 (s, 3H), 3.91 (s, 3H), 7.16 (s, 1H), 7.34-7.43 (m, 3H), 7.57 (s, 1H), 7.69 (d, J=9.1 Hz, 1H), 7.78-7.81 (m, 2H), 8.08 (dd, J=2.3, 8.8 Hz, 1H), 8.41 (s, 1H).

LCMS (ESI): calcd for $C_{20}H_{18}N_5O_3$ [M+H]$^+$ 376.1, found 376.1.

Example 8

1-Benzyl-2-{(E)-2-[3-methoxy-4-(4-methyl-imidazol-1-yl)-phenyl]-vinyl}-1H-benzimidazole

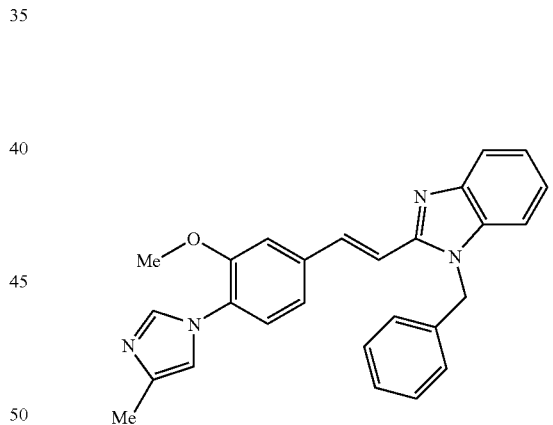

Aldehyde (175 mg, 0.81 mmol), phosphonium salt (504 mg, 0.97 mmol), LiOH.H$_2$O (102 mg, 2.43 mmol), THF (4.5 mL), and ethanol (1.5 mL) according the GP 2 gave the title compound (220 mg) as a yellow solid after chromatography on silica gel.

$^1$H (600 MHz, dmso-d6): 2.13 (s, 3H), 3.89 (s, 3H), 5.75 (s, 2H), 7.14 (s, 1H), 7.16-7.24 (m, 6H), 7.28-7.31 (m, 2H), 7.39 (d, J=7.9 Hz, 1H), 7.44-7.46 (m, 1H), 7.51 (d, J=7.8 Hz, 1H), 7.60-7.66 (m, 2H), 7.79 (s, 1H), 7.89 (s, 1H).

LCMS (ESI): calcd for $C_{27}H_{25}N_4O$ [M+H]$^+$ 421.2, found 421.2.

Example 9

1-Benzyl-5-chloro-2-{(E)-2-[3-methoxy-4-(4-methyl-imidazol-1-yl)-phenyl]-vinyl}-1H-benzimidazole

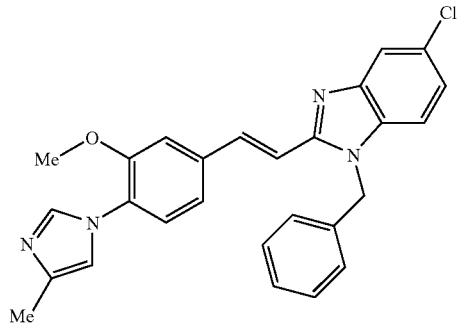

Aldehyde (150 mg, 0.69 mmol), phosphonium salt (658 mg, 0.83 mmol), LiOH.H$_2$O (87 mg, 2.08 mmol), THF (4.5 mL), and ethanol (1.5 mL) according the GP 2 gave the title compound (238 mg) as a yellow solid after chromatography on silica gel and recrystallization from ethyl acetate.

$^1$H (600 MHz, dmso-d6): 2.13 (s, 3H), 3.89 (s, 3H), 5.76 (s, 2H), 7.15-7.24 (m, 6H), 7.29-7.31 (m, 2H), 7.40 (d, J=7.1 Hz, 1H), 7.46-7.47 (m, 1H), 7.54 (d, J=8.8 Hz, 1H), 7.61-7.66 (m, 2H), 7.80 (s, 1H), 7.91 (s, 1H).

LCMS (ESI): calcd for C$_{27}$H$_{24}$ClN$_4$O [M+H]$^+$ 455.1, found 455.1.

Example 10

6-Chloro-2-{(E)-2-[3-methoxy-4-(4-methyl-imidazol-1-yl)-phenyl]-vinyl}-1H-benzimidazole

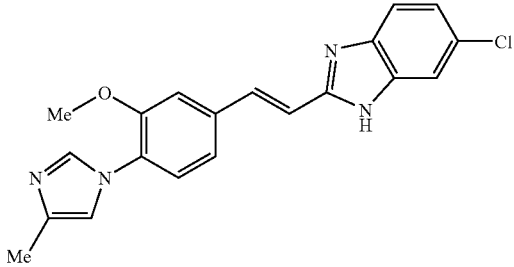

Aldehyde (150 mg, 0.69 mmol), phosphonium salt (386 mg, 0.83 mmol), LiOH.H$_2$O (87 mg, 2.08 mmol), THF (4.5 mL), and ethanol (1.5 mL) according the GP 2 gave the title compound (188 mg) as a yellow solid after recrystallization from ethyl acetate (12 mL).

$^1$H (600 MHz, dmso-d6): 2.13 (s, 3H), 3.90 (s, 3H), 7.15 (s, 1H), 7.16-7.20 (m, 1H), 7.31-7.33 (m, 2H), 7.40 (d, J=7.9 Hz, 1H), 7.49-7.71 (m, 5H), 7.80 (s, 1H).

LCMS (ESI): calcd for C$_{20}$H$_{18}$ClN$_4$O [M+H]$^+$ 365.1, found 365.1.

Example 11

2-{(E)-2-[3-Methoxy-4-(4-methyl-imidazol-1-yl)-phenyl]-vinyl}-1-methyl-1H-benzimidazole

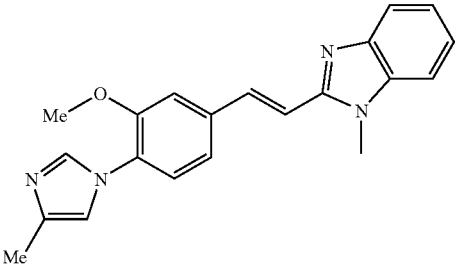

Aldehyde (100 mg, 0.46 mmol), phosphonium salt (270 mg, 0.56 mmol), LiOH.H$_2$O (58 mg, 1.39 mmol), THF (3 mL), and ethanol (1 mL) according the GP 2 gave the title compound (149 mg) as a colorless solid after recrystallization from ethyl acetate (10 mL).

$^1$H (600 MHz, dmso-d6): 2.14 (s, 3H), 3.91 (s, 3H), 3.95 (s, 3H), 7.16 (s, 1H), 7.19-7.23 (m, 2H), 7.40 (d, J=7.9 Hz, 1H), 7.46-7.48 (m, 1H), 7.52-7.59 (m, 3H), 7.65 (d, J=1.5 Hz, 1H), 7.80 (s, 1H), 7.85 (s, 1H).

LCMS (ESI): calcd for C$_{20}$H$_{21}$N$_4$O [M+H]$^+$ 345.1, found 345.1.

Example 12

5-[(E)-2-(5-Chloro-6-fluoro-1H-benzimidazol-2-yl)-vinyl]-2-(4-methyl-imidazol-1-yl)-phenol trifluoroacetate salt

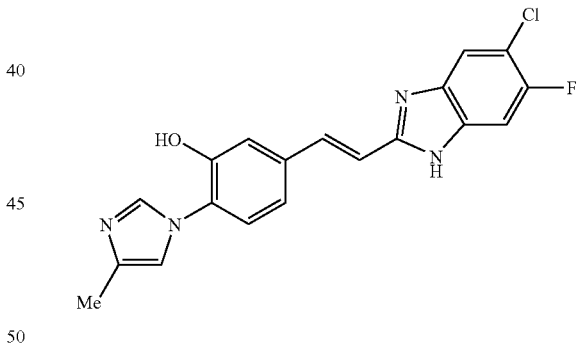

(E)-3-[3-Methoxy-4-(4-methyl-imidazol-1-yl)-phenyl]-acrylic acid (100 mg, 0.39 mmol) and 4-fluoro-5-chloro-benzene-1,2-diamine (62 mg, 0.39 mmol) were added to a 4-mL vial. Polyphosphoric acid (~1 ml) was added, the vial capped with a septum cap, and the reaction mixture heated to 200° C. for 3 h. The reaction was quenched with water and the precipitated solid collected. The residue was purified by preparative HPLC Reverse phase (C-18), eluting with Acetonitrile/Water+0.05% TFA, to give the product (14 mg) as a brown solid.

$^1$H (600 MHz, dmso-d6): 2.32 (s, 3H), 7.18 (d, J=16.4 Hz, 1H), 7.30 (d, J=1.8 Hz, 1H), 7.35 (dd, J=1.7, 8.2 Hz, 1H), 7.54 (d, J=8.2 Hz, 1H), 7.60 (d, J=9.4 Hz, 1H), 7.64-7.68 (m, 1H), 7.74-7.76 (m, 2H), 9.33 (s, 1H).

LCMS (ESI): calcd for C$_{19}$H$_{14}$ClFN$_4$O [M+H]$^+$ 369.1, found 369.1.

Example 13

1-Benzyl-2-{(E)-2-[3-methoxy-4-(4-methyl-imidazol-1-yl)-phenyl]-vinyl}-1H-imidazole

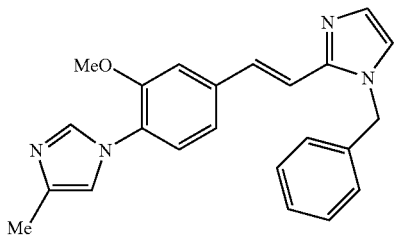

Aldehyde (120 mg, 0.56 mmol), phosphonium salt (374 mg, 0.67 mmol), LiOH.H$_2$O (70 mg, 1.76 mmol), THF (3 mL), and ethanol (1 mL) according the GP 2 gave the title compound (180 mg) as a colorless solid after recrystallization from ethyl acetate (10 mL).

$^1$H (600 MHz, dmso-d6): 2.12 (s, 3H), 3.86 (s, 3H), 5.42 (s, 2H), 7.00 (d, J=0.9 Hz, 1H), 7.10 (t, J=1.2 Hz, 1H), 7.20-7.21 (m, 2H), 7.24-7.35 (m, 7H), 7.40-7.42 (m, 2H), 7.75 (d, J=1.2 Hz, 1H).

LCMS (ESI): calcd for C$_{23}$H$_{23}$N$_4$O [M+H]$^+$ 371.2, found 371.2.

Example 14

5,6-Dichloro-1-ethyl-2-{(E)-2-[3-methoxy-4-(4-methyl-imidazol-1-yl)-phenyl]-vinyl}-1H-benzimidazole

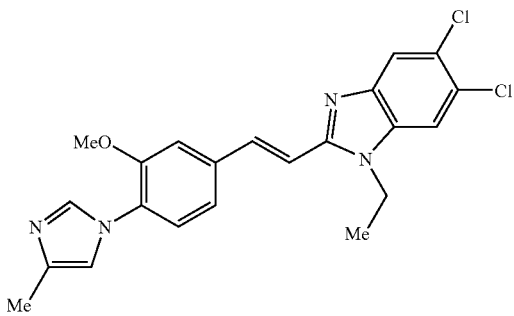

Aldehyde (120 mg, 0.56 mmol), phosphonate (243 mg, 0.67 mmol), LiOH.H$_2$O (70 mg, 1.67 mmol), THF (4.5 mL), and ethanol (1.5 mL) according the GP 3 gave the title compound (219 mg) as a yellow solid after recrystallization from ethyl acetate (10 mL).

$^1$H (600 MHz, dmso-d6): 1.30 (t, J=7.2 Hz, 3H), 2.14 (s, 3H), 3.91 (s, 3H), 4.50 (q, J=7.2 Hz, 2H), 7.16 (t, J=1.2 Hz, 1H), 7.41 (d, J=8.2 Hz, 1H), 7.50-7.53 (m, 2H), 7.64 (d, J=1.2 Hz, 1H), 7.81 (d, J=1.2 Hz, 1H), 7.84 (s, 1H), 7.92 (d, J=15.6 Hz, 1H), 7.99 (s, 1H).

LCMS (ESI): calcd for C$_{22}$H$_{21}$Cl$_2$N$_4$O [M+H]$^+$ 427.1, found 427.1.

Example 15

3-(2,3-Dichloro-phenyl)-5-{(E)-2-[3-methoxy-4-(4-methyl-imidazol-1-yl)-phenyl]-vinyl}-1,2,4-oxadiazole trifluoroacetate salt

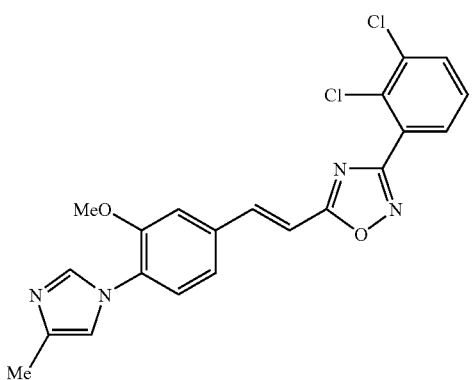

(2E)-3-[3-methoxy-4-(4-methyl-1H-imidazol-1-yl)phenyl]acrylic acid (64.5 mg, 0.250 mmol), carbonyl di-imidazole (44.5 mg, 0.275 mmol), and DMF (1.325 ml) were added to a 4 ml scintillation vial and allowed to stir for 30 minutes at room temperature. 2,3-Dichloro-N'-hydroxybenzenecarboximidamide (56.3 mg, 0.275 mmol) was added and the reaction mixture was allowed to stir overnight at room temperature. The contents of the vial were transferred to a 0.5-2.0 ml microwave vial and an additional 1.1 equivalents of carbonyl di-imidazole (44.5 mg, 0.275 mmol) were added. The vial was sealed and microwaved at 160° C. for 11 minutes.

Purification by reverse phase chromatography (5%-80% MeCN in Water) gave 3-(2,3-dichlorophenyl)-5-{(E)-2-[3-methoxy-4-(4-methyl-1H-imidazol-1-yl)phenyl]vinyl}-1,2,4-oxadiazole as a white solid.

LCMS (ESI): calcd for C$_{21}$H$_{17}$Cl$_2$N$_4$O$_2$ [M+H]$^+$ 426.1, found 426.1.

Example 16

2-{(E)-2-[3-Methoxy-4-(4-methyl-imidazol-1-yl)-phenyl]-vinyl}-3H-benzimidazole-5-sulfonic acid diethylamide trifluoroacetate salt

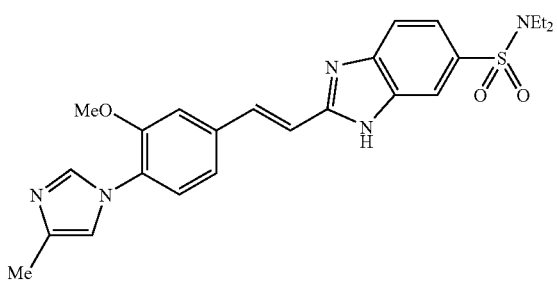

Aldehyde (120 mg, 0.56 mmol), phosphonium salt (376 mg, 0.67 mmol), LiOH.H$_2$O (70 mg, 1.67 mmol), THF (3 mL), and ethanol (1 mL) according the GP 2 gave the title compound (70 mg) as a colorless solid after reversed phase purification.

$^1$H (600 MHz, dmso-d6): 1.02 (t, J=7.1 Hz, 6H), 2.33 (s, 3H), 3.15 (q, J=7.1 Hz, 4H), 3.95 (s, 3H), 7.45-7.51 (m, 2H), 7.59-7.63 (m, 2H), 7.67 (s, 1H), 7.71-7.74 (m, 2H), 7.80 (d, J=16.4 Hz, 1H), 7.94 (d, J=1.4 Hz, 1H), 9.34 (d, J=1.5 Hz, 1H).

LCMS (ESI): calcd for $C_{24}H_{28}N_5O_3S$ [M+H]$^+$ 466.2, found 466.2.

Example 17

2-{(E)-2-[3-Methoxy-4-(4-methyl-imidazol-1-yl)-phenyl]-vinyl}-3H-quinazolin-4-one trifluoroacetate salt

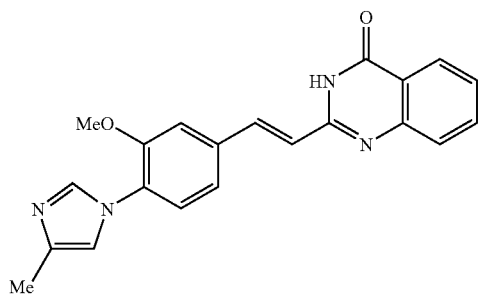

Aldehyde (150 mg, 0.69 mmol), phosphonate (226 mg, 0.76 mmol), LiOH.H$_2$O (87 mg, 2.08 mmol), THF (4.5 mL), and ethanol (1.5 mL) according the GP 3 gave the title compound (253 mg) as a yellow solid after revered phase purification.

$^1$H (600 MHz, dmso-d6): 2.33 (s, 3H), 3.93 (s, 3H), 7.18 (d, J=16.4 Hz, 1H), 7.41 (dd, J=1.5, 8.2 Hz, 1H), 7.49 (dt, J=1.2, 8.0 Hz, 1H), 7.63-7.67 (m, 3H), 7.73 (s, 1H), 7.80-7.82 (m, 1H), 7.99 (d, J=16.1 Hz, 1H), 8.10 (dd, J=1.1, 7.9 Hz, 1H), 9.30 (d, J=1.5 Hz, 1H).

LCMS (ESI): calcd for $C_{21}H_{19}N_4O_2$ [M+H]$^+$ 359.1, found 359.1.

Example 18

7-Chloro-2-{(E)-2-[3-methoxy-4-(4-methyl-imidazol-1-yl)-phenyl]-vinyl}-3H-quinazolin-4-one trifluoroacetate salt

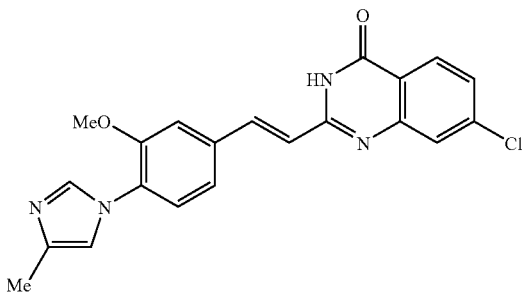

Aldehyde (400 mg, 1.85 mmol), phosphonate (612 mg, 1.85 mmol), LiOH.H$_2$O (233 mg, 2.08 mmol), THF (12 mL), and ethanol (4 mL) according the GP 3 gave the title compound (520 mg) as a yellow solid after revered phase purification.

$^1$H (600 MHz, dmso-d6): 2.31 (s, 3H), 3.93 (s, 3H), 7.15 (d, J=16.2 Hz, 1H), 7.40 (dd, J=1.5, 8.3 Hz, 1H), 7.52 (dd, J=1.1, 8.5 Hz, 1H), 7.62-7.63 (m, 1H), 7.68-7.69 (m, 1H), 7.99 (d, J=16.2 Hz, 1H), 8.09 (d, J=8.5 Hz, 1H), 9.20 (br s, 1H).

LCMS (ESI): calcd for $C_{21}H_{18}ClN_4O_2$ [M+H]$^+$ 393.1, found 393.1.

Example 19

5,7-Dichloro-3-(2,6-dimethyl-phenyl)-2-{(E)-2-[3-methoxy-4-(4-methyl-imidazol-1-yl)-phenyl]-vinyl}-3H-quinazolin-4-one

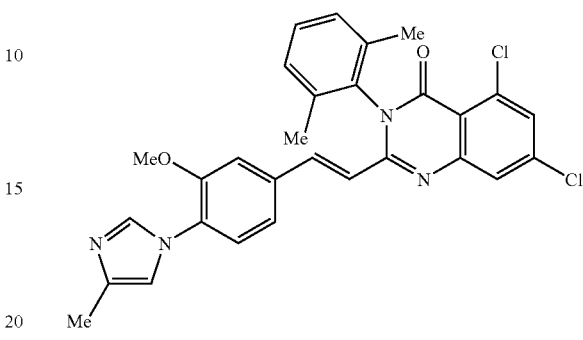

Aldehyde (70 mg, 0.32 mmol), phosphonate (182 mg, 0.39 mmol), LiOH.H$_2$O (41 mg, 0.97 mmol), THF (2.5 mL), and ethanol (1 mL) according the GP 3 gave the title compound (77 mg) as a yellow solid.

$^1$H (600 MHz, dmso-d6): 1.99 (s, 6H), 2.11 (s, 3H), 3.79 (s, 3H), 6.22 (d, J=15.5 Hz, 1H), 6.97 (dd, J=1.5, 7.8 Hz, 1H), 7.10 (s, 1H), 7.29 (d, J=1.5 Hz, 1H), 7.32-7.34 (m, 3H), 7.39-7.41 (m, 1H), 7.76 (d, J=1.6 Hz, 1H), 8.03 (d, J=15.5 Hz, 1H), 8.08 (d, J=2.3 Hz, 1H), 8.24 (d, J=2.3 Hz, 1H).

LCMS (ESI): calcd for $C_{29}H_{25}Cl_2N_4O_2$ [M+H]$^+$ 531.1, found 531.1.

Example 20

2-{(E)-2-[3-Methoxy-4-(4-methyl-imidazol-1-yl)-phenyl]-vinyl}-5-methyl-4-oxo-3,4-dihydro-thieno[2,3-d]pyrimidine-6-carboxylic acid diethylamide

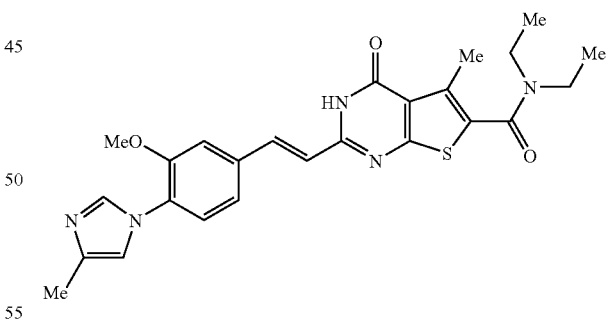

Aldehyde (120 mg, 0.55 mmol), phosphonate (277 mg, 0.67 mmol), LiOH.H$_2$O (70 mg, 1.67 mmol), THF (4.5 mL), and ethanol (1.5 mL) according the GP 3 gave the title compound (131 mg) as a yellow solid.

$^1$H (600 MHz, dmso-d6): 1.07-1.10 (m, 6H), 2.13 (s, 3H), 2.37 (s, 3H), 3.34-3.36 (m, 4H), 3.87 (s, 3H), 7.02 (d, J=15.8 Hz, 1H), 7.14 (s, 1H), 7.28 (d, J=7.9 Hz, 1H), 7.38 (d, J=7.9 Hz, 1H), 7.48 (s, 1H), 7.78-7.81 (m, 2H).

LCMS (ESI): calcd for $C_{25}H_{28}N_5O_3S$ [M+H]$^+$ 478.2, found 478.2.

Example 21

2-{(E)-3-[3-Methoxy-4-(4-methyl-imidazol-1-yl)-phenyl]-vinyl}-3,5,6,7-tetrahydro-cyclopenta[4,5]thieno[2,3-d]pyrimidin-4-one trifluoroacetate salt

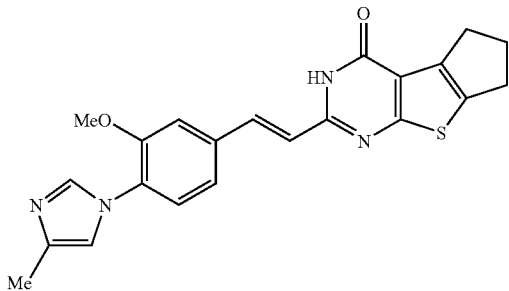

Aldehyde (150 mg, 0.55 mmol), phosphonate (228 mg, 0.67 mmol), LiOH.H$_2$O (70 mg, 1.67 mmol), THF (4.5 mL), and ethanol (1.5 mL) according the GP 3 gave the title compound (130 mg) as a yellow solid after revered phase purification.

$^1$H (600 MHz, dmso-d6): 2.32 (s, 3H), 2.35-2.40 (m, 2H), 2.91 (d, J=7.3 Hz, 4H), 3.91 (s, 3H), 7.12 (d, J=16.1 Hz, 1H), 7.38 (dd, J=1.8, 8.3 Hz, 1H), 7.60-7.62 (m, 2H), 7.71 (s, 1H), 7.93 (d, J=16.2 Hz, 1H), 9.27 (br s, 1H).

LCMS (ESI): calcd for C$_{22}$H$_{21}$N$_4$O$_2$S [M+H]$^+$ 405.1, found 405.1.

Example 22

2-{(E)-3-[3-Methoxy-4-(4-methyl-imidazol-1-yl)-phenyl]-vinyl}-6-phenyl-3H-thieno[2,3-d]pyrimidin-4-one

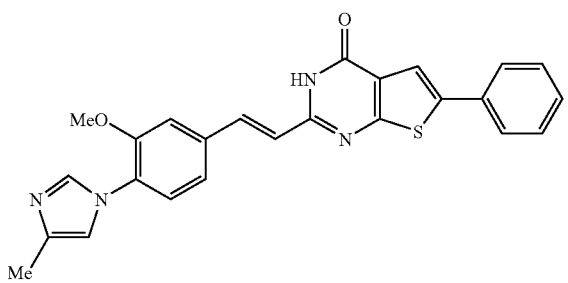

Aldehyde (120 mg, 0.55 mmol), phosphonate (252 mg, 0.67 mmol), LiOH.H$_2$O (70 mg, 1.67 mmol), THF (4.5 mL), and ethanol (1.5 mL) according the GP 3 gave the title compound (222 mg) as a yellow solid.

$^1$H (600 MHz, dmso-d6): 2.13 (s, 3H), 3.88 (s, 3H), 7.03 (d, J=16.1 Hz, 1H), 7.13 (s, 1H), 7.26-7.28 (m, 1H), 7.35-7.41 (m, 4H), 7.48 (s, 1H), 7.58 (s, 1H), 7.64-7.67 (m, 2H), 7.74-7.77 (m, 2H).

LCMS (ESI): calcd for C$_{25}$H$_{21}$N$_4$O$_2$S [M+H]$^+$ 441.1, found 441.1.

Example 23

2-{(E)-3-[3-Methoxy-4-(4-methyl-imidazol-1-yl)-phenyl]-vinyl}-5-methyl-4-oxo-3,4-dihydro-thieno[2,3-d]pyrimidine-6-carboxylic acid propyl ester trifluoroacetate salt

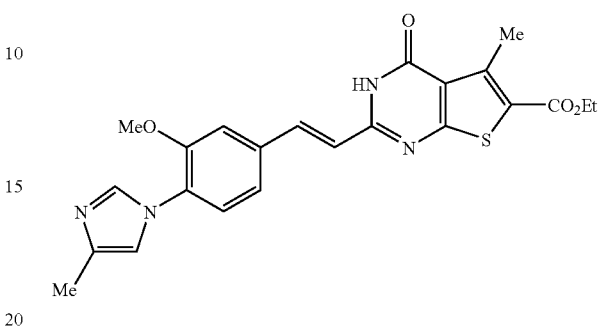

Aldehyde (120 mg, 0.55 mmol), phosphonate (252 mg, 0.67 mmol), LiOH.H$_2$O (70 mg, 1.67 mmol), THF (4.5 mL), and ethanol (1.5 mL) according the GP 3 gave the title compound (222 mg) as a yellow solid after reversed phase purification.

$^1$H (600 MHz, dmso-d6): 1.29 (t, J=7.1 Hz, 3H), 2.31 (s, 3H), 2.83 (s, 3H), 3.91 (s, 3H), 4.29 (q, J=7.1 Hz, 2H), 7.15 (d, J=16.1 Hz, 1H), 7.41-7.43 (m, 1H), 7.62-7.68 (m, 3H), 8.03 (d, J=16.2 Hz, 1H), 9.20 (br s, 1H).

LCMS (ESI): calcd for C$_{23}$H$_{22}$N$_4$O$_4$S [M+H]$^+$ 451.1, found 451.1.

Example 24

2-{(E)-2-[3-Methoxy-4-(4-methyl-imidazol-1-yl)-phenyl]-vinyl}-3H-benzofuro[2,3-d]pyrimidin-4-one trifluoroacetate salt

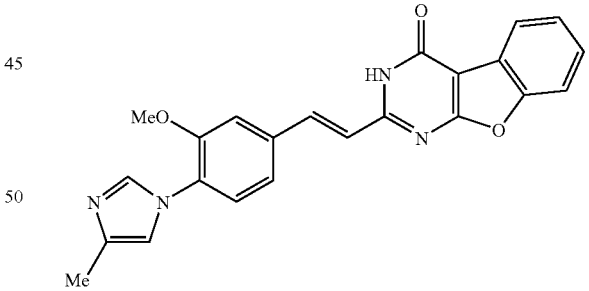

Aldehyde (120 mg, 0.56 mmol), phosphonate (187 mg, 0.56 mmol), LiOH.H$_2$O (70 mg, 1.67 mmol), THF (4.5 mL), and ethanol (1.5 mL) according the GP 3 gave the title compound (130 mg) as a colorless solid after reversed phase purification.

$^1$H (600 MHz, dmso-d6): 2.31 (s, 3H), 3.94 (s, 3H), 7.25 (d, J=16.2 Hz, 1H), 7.42 (dd, J=1.8, 8.2 Hz, 1H), 7.52 (t, J=7.5 Hz, 1H), 7.62-7.70 (m, 4H), 7.84 (d, J=8.5 Hz, 1H), 8.01 (d, J=16.1 Hz, 1H), 8.05 (d, J=7.9 Hz, 1H), 9.17 (br s, 1H).

LCMS (ESI): calcd for C$_{23}$H$_{19}$N$_4$O$_3$ [M+H]$^+$ 399.1, found 399.1.

Example 25

2-{(E)-2-[3-Methoxy-4-(4-methyl-imidazol-1-yl)-phenyl]-vinyl}-7-trifluoromethyl-3H-quinazolin-4-one trifluoroacetate salt

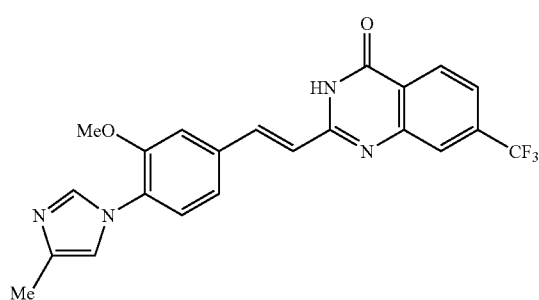

Aldehyde (120 mg, 0.56 mmol), phosphonate (243 mg, 0.67 mmol), LiOH.H$_2$O (70 mg, 1.67 mmol), THF (4.5 mL), and ethanol (1.5 mL) according the GP 3 gave the title compound (36 mg) as a colorless solid after reversed phase purification as well as the free base (25 mg).

$^1$H (600 MHz, dmso-d6): 2.14 (s, 3H), 3.90 (s, 3H), 7.08 (d, J=16.1 Hz, 1H), 7.16 (s, 1H), 7.31 (dd, J=1.4, 7.9 Hz, 1H), 7.45 (d, J=8.2 Hz, 1H), 7.51 (s, 1H), 7.74 (dd, J=1.4, 8.2 Hz, 1H), 7.82 (d, J=1.1 Hz, 1H), 7.92 (s, 1H), 8.02 (d, J=16.1 Hz, 1H), 8.27 (d, J=8.2 Hz, 1H).

LCMS (ESI): calcd for C$_{22}$H$_{18}$F$_3$N$_4$O$_2$ [M+H]$^+$ 427.1, found 427.1.

Example 26

7-Bromo-2-{(E)-2-[3-methoxy-4-(4-methyl-imidazol-1-yl)-phenyl]-vinyl}-3H-quinazolin-4-one trifluoroacetate salt

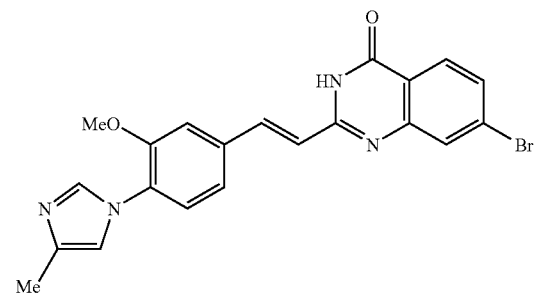

Aldehyde (140 mg, 0.65 mmol), phosphonate (243 mg, 0.65 mmol), LiOH.H$_2$O (82 mg, 1.94 mmol), THF (4.5 mL), and ethanol (1.5 mL) according the GP 3 gave the title compound (210 mg) as a yellow solid after reversed phase purification.

$^1$H (600 MHz, dmso-d6): 2.31 (s, 3H), 3.93 (s, 3H), 7.15 (d, J=16.1 Hz, 1H), 7.40 (dd, J=1.4, 8.2 Hz, 1H), 7.62-7.69 (m, 4H), 7.83 (d, J=1.7 Hz, 1H), 7.98-8.02 (m, 2H), 9.19 (br s, 1H).

LCMS (ESI): calcd for C$_{21}$H$_{18}$BrN$_4$O$_2$ [M+H]$^+$ 437.1, found 437.1.

Example 27

5,7-Dichloro-2-{(E)-2-[3-methoxy-4-(4-methyl-imidazol-1-yl)-phenyl]-vinyl}-3H-quinazolin-4-one trifluoroacetate salt

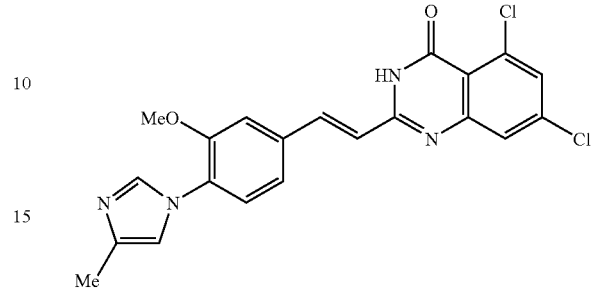

Aldehyde (140 mg, 0.65 mmol), phosphonate (236 mg, 0.65 mmol), LiOH.H$_2$O (82 mg, 1.94 mmol), THF (4.5 mL), and ethanol (1.5 mL) according the GP 3 gave the title compound (210 mg) as a yellow solid after reversed phase purification.

$^1$H (600 MHz, dmso-d6): 2.31 (s, 3H), 3.93 (s, 3H), 7.11 (d, J=16.1 Hz, 1H), 7.40 (dd, J=1.4, 8.2 Hz, 1H), 7.61-7.68 (m, 4H), 7.99 (d, J=16.1 Hz, 1H), 9.19 (br s, 1H).

LCMS (ESI): calcd for C$_{21}$H$_{17}$Cl$_2$N$_4$O$_2$ [M+H]$^+$ 427.0, found 427.0.

Example 28

2-{(E)-2-[3-Methoxy-4-(4-methyl-imidazol-1-yl)-phenyl]-vinyl}-3H-benzo[g]quinazolin-4-one trifluoroacetate salt

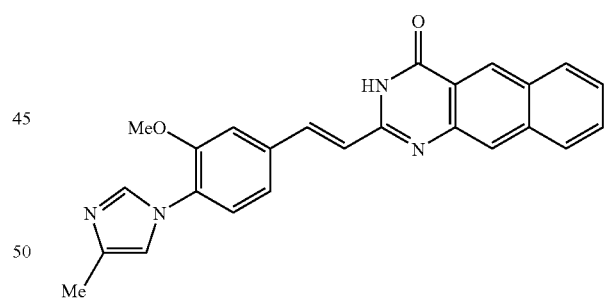

Aldehyde (140 mg, 0.65 mmol), phosphonate (224 mg, 0.65 mmol), LiOH.H$_2$O (82 mg, 1.94 mmol), THF (4.5 mL), and ethanol (1.5 mL) according the GP 3 gave the title compound (338 mg) as an orange solid after reversed phase purification.

$^1$H (600 MHz, dmso-d6): 2.33 (s, 3H), 3.95 (s, 3H), 7.21 (d, J=16.4 Hz, 1H), 7.43 (dd, J=1.5, 8.2 Hz, 1H), 7.56-7.59 (m, 1H), 7.64-7.67 (m, 3H), 7.75 (s, 1H), 8.02 (d, J=16.1 Hz, 1H), 8.10 (d, J=8.5 Hz, 1H), 8.19 (d, J=8.2 Hz, 1H), 8.22 (s, 1H), 8.82 (s, 1H), 9.35 (br s, 1H).

LCMS (ESI): calcd for C$_{25}$H$_{21}$N$_4$O$_2$ [M+H]$^+$ 409.1, found 409.1.

Example 29

7-Methanesulfonyl-2-{(E)-2-[3-methoxy-4-(4-methyl-imidazol-1-yl)-phenyl]-vinyl}-3H-quinazolin-4-one trifluoroacetate salt

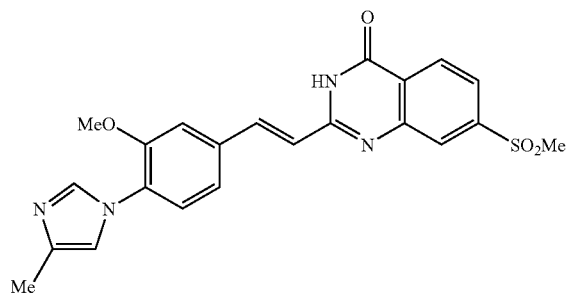

Aldehyde (140 mg, 0.65 mmol), phosphonate (242 mg, 0.65 mmol), LiOH.H₂O (82 mg, 1.94 mmol), THF (4.5 mL), and ethanol (1.5 mL) according the GP 3 gave the title compound (150 mg) as a yellow solid after reversed phase purification.

¹H (600 MHz, dmso-d6): 2.33 (s, 3H), 2.51 (s, 3H), 3.94 (s, 3H), 7.20 (d, J=16.2 Hz, 1H), 7.43 (dd, J=1.5, 8.0 Hz, 1H), 7.64-7.65 (m, 2H), 7.73 (t, J=1.1 Hz, 1H), 7.94 (dd, J=1.7, 8.2 Hz, 1H), 8.06 (d, J=15.8 Hz, 1H), 8.12 (d, J=1.8 Hz, 1H), 8.32 (d, J=8.3 Hz, 1H), 9.29 (br s, 1H).

LCMS (ESI): calcd for $C_{22}H_{21}N_4O_4S$ [M+H]⁺ 437.1, found 437.1.

Example 30

4-Amino-2-{(E)-2-[3-methoxy-4-(4-methyl-imidazol-1-yl)-phenyl]-vinyl}-6-methyl-furo[2,3-d]pyrimidine-5-carboxylic acid ethyl ester trifluoroacetate salt

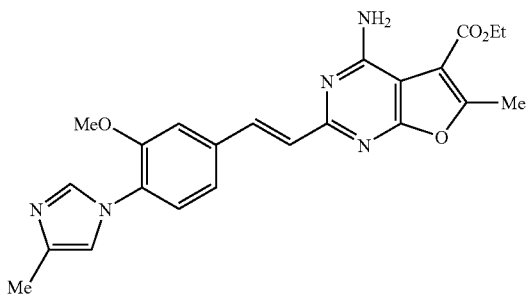

Aldehyde (140 mg, 0.65 mmol), phosphonate (240 mg, 0.65 mmol), LiOH.H₂O (82 mg, 1.94 mmol), THF (4.5 mL), and ethanol (1.5 mL) according the GP 3 gave the title compound (170 mg) as a yellow solid after reversed phase purification.

¹H (600 MHz, dmso-d6): 1.34 (t, J=7.2 Hz, 3H), 2.33 (s, 3H), 3.93 (s, 3H), 4.36 (q, J=7.0 Hz, 2H), 7.24 (d, J=15.8 Hz, 1H), 7.44 (dd, J=1.5, 8.4 Hz, 1H), 7.56-7.66 (m, 4H), 7.72 (t, J=1.3 Hz, 1H), 7.82 (d, J=15.8 Hz, 1H), 9.32 (s, 1H).

LCMS (ESI): calcd for $C_{22}H_{21}N_4O_4S$ [M+H]⁺ 434.1, found 434.1.

Examples 31-46

The following compounds were additionally prepared according to GP1:

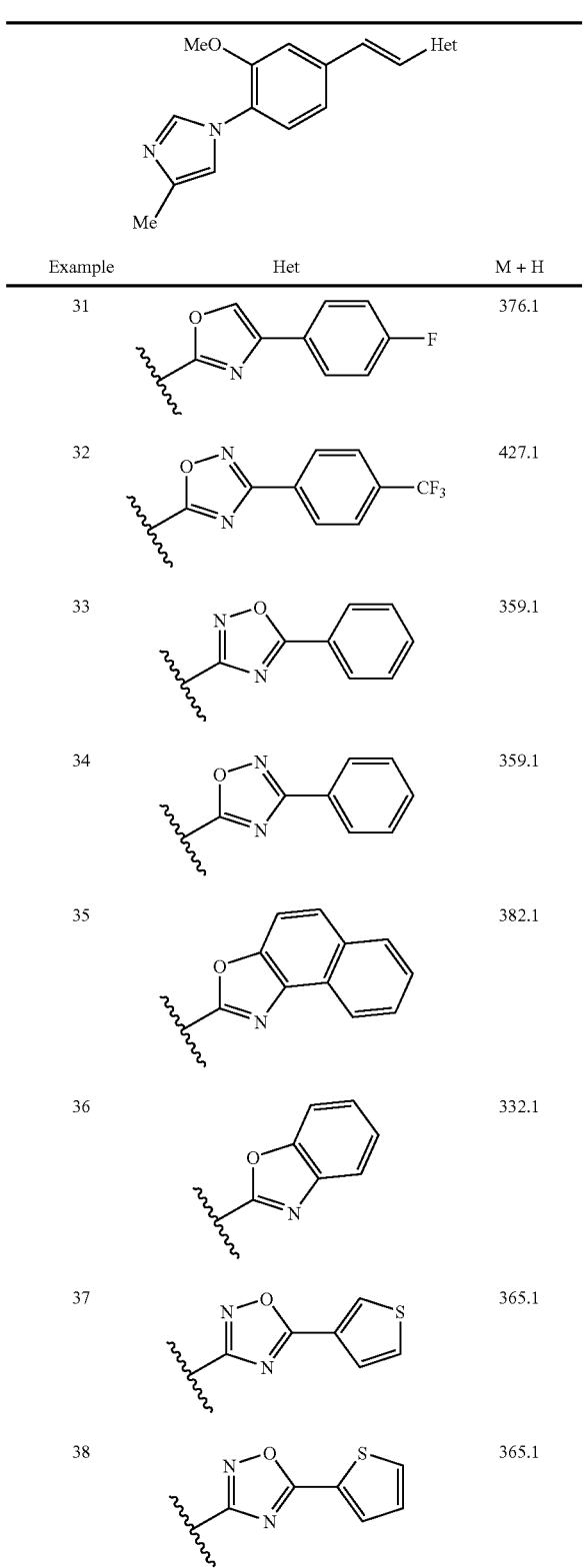

-continued
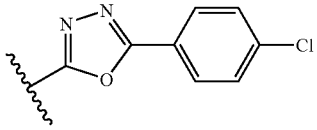
| Example | Het | M + H |
|---|---|---|
| 39 | 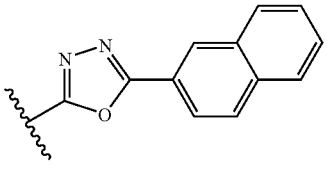 | 393.1 |
| 40 | 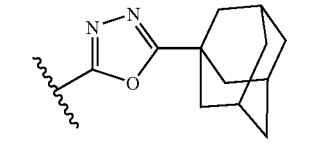 | 409.1 |
| 41 | 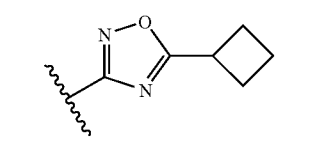 | 417.1 |
| 42 | 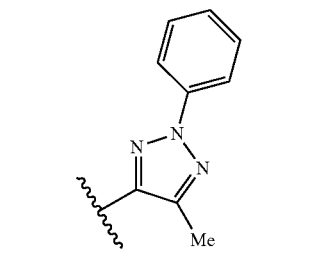 | 337.1 |
| 43 | 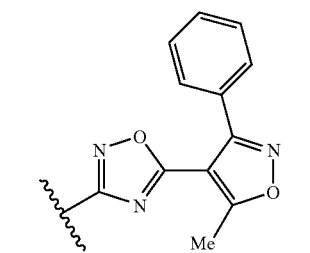 | 372.1 |
| 44 | 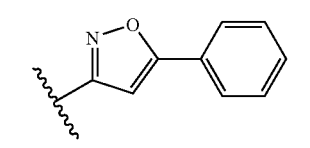 | 440.1 |
| 45 | 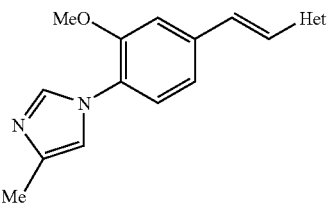 | 358.1 |
-continued
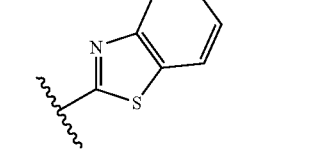
| Example | Het | M + H |
|---|---|---|
| 46 | 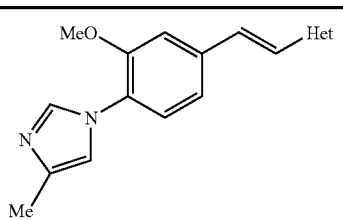 | 348.1 |
Examples 47-61
The following compounds were additionally prepared according to GP3:
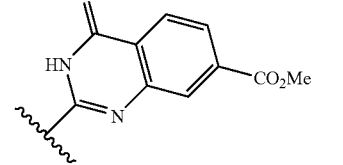
| Example | Het | M + H |
|---|---|---|
| 47 | 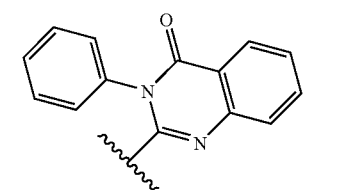 | 417.1 |
| 48 | 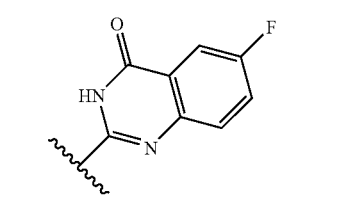 | 435.1 |
| 49 | | 377.1 |

| Example | Het | M + H |
|---|---|---|
| 50 | 7-chloro-quinazolin-4(3H)-one-2-yl | 393.1 |
| 51 | 6,7-difluoro-quinazolin-4(3H)-one-2-yl | 395.1 |
| 52 | 5-fluoro-quinazolin-4(3H)-one-2-yl | 377.1 |
| 53 | 8-methyl-quinazolin-4(3H)-one-2-yl | 373.1 |
| 54 | 3-methyl-quinazolin-4(3H)-one-2-yl | 373.1 |
| 55 | 1,1-dioxo-4H-benzo[1,2,4]thiadiazin-3-yl | 395.1 |
| 56 | 6,8-dibromo-quinazolin-4(3H)-one-2-yl | 514.9 |
| 57 | 7-ethoxycarbonyl-quinazolin-4(3H)-one-2-yl | 431.1 |
| 58 | 7-pyrrolidin-1-yl-quinazolin-4(3H)-one-2-yl | 428.1 |
| 59 | 5-methyl-thieno[2,3-d]pyrimidin-4(3H)-one-2-yl | 379.1 |
| 60 | 5,6-dimethyl-thieno[2,3-d]pyrimidin-4(3H)-one-2-yl | 393.1 |
| 61 | 6-acetyl-5-methyl-thieno[2,3-d]pyrimidin-4(3H)-one-2-yl | 421.1 |

Examples 62-68

The following compounds were additionally prepared according to GP4:

[Structure: MeO and Het substituents on phenyl ring with 4-methylimidazol-1-yl group]

| Example | Het | M + H |
|---------|-----|-------|
| 62 | oxadiazole-pyridine-CF₃ | 428.1 |
| 63 | oxadiazole-phenyl-OMe | 389.1 |
| 64 | oxadiazole-naphthyl-OMe | 439.1 |
| 65 | oxadiazole-phenyl-pyrrolyl | 424.1 |
| 66 | oxadiazole-phenyl-CF₃ | 427.1 |
| 67 | oxadiazole-phenyl-Cl | 393.1 |
| 68 | oxadiazole-phenyl-Br | 437.0 |

Examples 69-75

The following compounds were additionally prepared as for 6-fluoro-2-{(E)-2-[3-methoxy-4-(4-methyl-imidazol-1-yl)-phenyl]-vinyl}-1H-benzimidazole (Example 6).

[Structure: MeO and Het substituents on phenyl ring with 4-methylimidazol-1-yl group]

| Example | Het | M + H |
|---------|-----|-------|
| 69 | benzimidazole-Me | 345.1 |
| 70 | benzimidazole-diMe | 359.1 |
| 71 | benzimidazole-diF | 367.1 |
| 72 | benzimidazole-diF | 367.1 |
| 73 | benzimidazole-diF | 367.1 |
| 74 | benzimidazole-OMe | 361.1 |

-continued

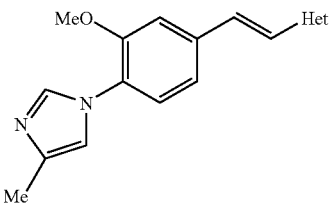

| Example | Het | M + H |
|---|---|---|
| 75 | 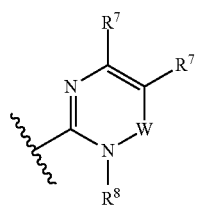 | 371.1 |

What is claimed is:

1. A compound of formula I:

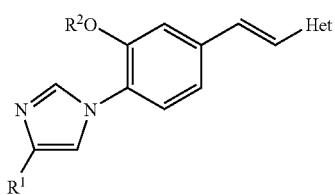

or a pharmaceutically acceptable salt thereof; wherein:
$R^1$ represents H, $C_{1-6}$alkyl, $C_{3-6}$cycloalkyl or $C_{2-6}$alkenyl;
$R^2$ represents $C_{1-6}$alkyl, $C_{3-6}$cycloalkyl or $C_{2-6}$alkenyl;
Het represents:

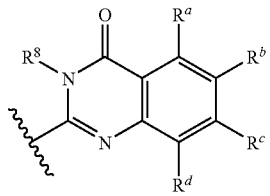

W represents C=O or $SO_2$;
each $R^7$ independently represents H or a substituent selected from:
alkyl, alkenyl, alkynyl, cycloalkyl and cycloalkylalkyl groups, all of up to 10 carbon atoms, phenyl, naphthyl, 5- or 6-membered heterocyclyl, halogen, CN, $NO_2$, $CF_3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$;
where said alkyl, alkenyl, alkynyl, cycloalkyl and cycloalkylalkyl groups bear 0-1 substituents selected from halogen, CN, $NO_2$, $CF_3$, $OR^6$, $COR^6$, $CO_2R^6$, $OCOR^5$, $N(R^6)_2$, $CON(R^6)_2$, $SR^5$, $S_2R^5$, and $SO_2N(R^6)_2$;
and said phenyl, naphthyl and 5- or 6-membered heterocyclyl bear 0-3 substituents selected from halogen, CN, $NO_2$, $R^5$, $OR^6$, $COR^6$, $CO_2R^6$ $OCOR^5$, $N(R^6)_2$, CON$(R^6)_2$, $SR^5$, $SO_2R^5$, and $SO_2N(R^6)_2$ ;

or two $R^7$ groups attached to adjacent ring atoms may together represent a fused ring system consisting of a phenyl or a 5- or 6-membered heteroaryl ring which is optionally fused to a further 5- or 6-membered carbocyclic or heterocyclic ring, said fused ring system bearing 0-3 substituents selected from halogen, CN, $NO_2$, $R^3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$; and
$R^8$ represents H, $C_{1-6}$alkyl, $C_{3-6}$cycloalkyl, $C_{3-6}$cycloalkyl, $C_{1-4}$alkyl, phenyl or benzyl wherein said phenyl and benzyl bear 0-2 substituents selected from halogen, $CF_3$ and $C_{1-4}$ alkyl;
$R^3$ represents $C_{1-6}$alkyl, $C_{3-6}$cycloalkyl, $c_{2-6}$alkenyl, phenyl, benzyl or $CF_3$;
$R^4$ represents H or $R^3$ or two $R^4$ groups attached to the same nitrogen atom optionally complete a heterocyclic group of up to 7 ring atoms which bears 0-3 substituents selected from halogen, $CF_3$, $C_{1-4}$alkyl, $C_{1-4}$alkoxy and $C_{1-4}$alkoxycarbonyl;
$R^5$ represents $C_{1-6}$alkyl, phenyl or $CF_3$; and
$R^6$ represents H or $R^5$ or two $R^6$ groups attached to the same nitrogen atom optionally complete a heterocyclic group of up to 7 ring atoms which bears 0-3 substituents selected from halogen, $CF_3$, $C_{1-4}$alkyl, $C_{1-4}$alkoxy and $C_{1-4}$alkoxycarbonyl.

2. A compound according to claim 1 or a pharmaceutically acceptable salt thereof wherein W represents C=O.

3. A compound according to claim 1 or a pharmaceutically acceptable salt thereof wherein Het represents:

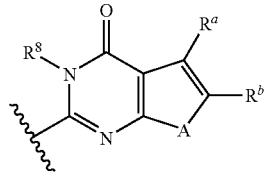

wherein $R^a$, $R^b$, $R^c$ and $R^d$ independently represent H, halogen, CN, $NO_2$, $R^3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$; or $R^a$ together with $R^b$, or $R^b$ together with $R^c$ or $R^c$ together with $R^d$ represents a fused 5- or 6-membered carbocyclic or heterocyclic ring; with the proviso that at least one of $R^a$, $R^b$, $R^c$ and $R^d$ is H.

4. A compound according to claim 3 or a pharmaceutically acceptable salt thereof wherein $R^a$, $R^b$, $R^c$ and $R^d$ independently represent H, halogen, $CF_3$, $C_{0-1}$alkyl, $C_{1-4}$alkoxy, $C_{1-4}$alkoxycarbonyl, $C_{1-4}$alkylsulfonyl or $C_{1-4}$alkylcarbonyl, provided at least one of $R^a$, $R^b$, $R^c$ and $R^d$ is H.

5. A compound according to claim 1 or a pharmaceutically acceptable salt thereof wherein Het represents:

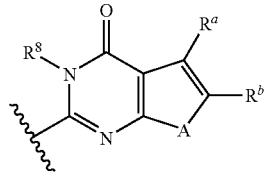

where A represents O or S;
$R^a$ and $R^b$ independently represent H, halogen, CN, $NO_2$, $R^3$, $OR^4$, $COR^4$, $CO_2R^4$, $OCOR^3$, $N(R^4)_2$, $CON(R^4)_2$, $SR^3$, $SO_2R^3$, and $SO_2N(R^4)_2$; or $R^a$ together with $R^b$ represents a fused 5- or 6-membered carbocyclic or heterocyclic ring.

6. A compound according to claim 5 or a pharmaceutically acceptable salt thereof wherein $R^a$ and $R^b$ independently represent H, halogen, $CF_3$, $C_{1-4}$alkyl, phenyl, $C_{1-4}$alkylcarbonyl, $C_{1-4}$alkoxy, $C_{1-4}$alkoxycarbonyl, $C_{1-4}$alkoxylsulfonyl, or di($C_{1-4}$alkyl)aminocarbonyl, or together represent a fused 5- or 6-membered carbocyclic or heterocyclic ring.

7. A pharmaceutical composition comprising a compound of formula I as defined in claim 1, or a pharmaceutically acceptable salt thereof, and a pharmaceutically acceptable carrier.

* * * * *